April 19, 1960 C. L. HAGLER Plant Pat. 1,935
NECTARINE TREE
Filed Nov. 17, 1958
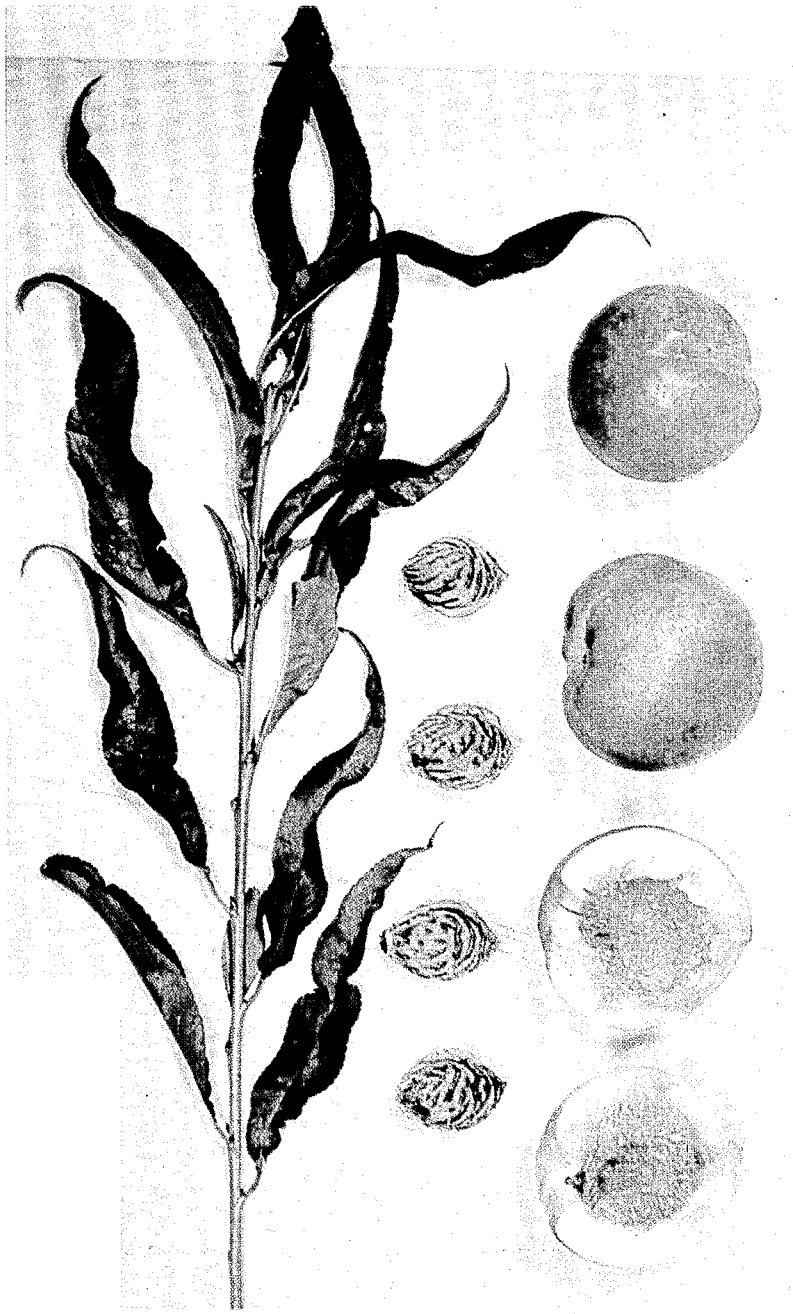
INVENTOR
C. L. Hagler
BY Robb & Robb
ATTORNEYS United States Patent Office Plant Pat. 1,935
Patented Apr. 19, 1960

1,935

NECTARINE TREE

Clinton L. Hagler, Visalia, Calif.

Application November 17, 1958, Serial No. 774,568

1 Claim. (Cl. 47—62)

The present invention relates to a new and distinct variety of nectarine tree of the yellow-fleshed clingstone fruit type, which was discovered by me as a sport of the variety "Le Grand" (Plant Patent No. 549) in my cultivated orchard near Visalia, Tulare County, California.

At the time of my discovery of the sport referred to above, my attention was initially attracted thereto by the presence of fruit on a "Le Grand" tree which was materially different from the usual fruit of that variety, as evidenced by its higher coloring and darker red texture interlined with gold. On closer examination and comparison of the fruit with that of the regular "Le Grand" variety, I found that the "Le Grand" tree had sported, and I thereupon promptly took steps to preserve the sport, keep it under close observation, and to later asexually reproduce the same.

Continued observations of the original sport, and asexual reproductions thereof as made by budding under my direction and supervision on my property referred to above near Visalia, California, showed that the new sport was definitely distinguished from the "Le Grand" variety, as well as from all other varieties known to me, by having the following unique combination of principal characteristics, among others:

(1) Leaves which are more crinkly than those of "Le Grand" and which have a tendency to roll along the edges;

(2) Blossoms which have more color than those of "Le Grand";

(3) Fruit which sizes and colors more rapidly than the fruit of "Le Grand," and which is larger, more highly colored, and has a more waxy sheen to the color;

(4) A fruit form which is not so truncated at the base and apex ends as the fruit of "Le Grand," but is more rounded and elongated;

(5) A fruit-ripening habit about 10 days to 2 weeks later than "Le Grand," but about one week to 10 days earlier than "Late Le Grand" (Plant Patent No. 1035);

(6) A uniform ripening habit of the fruit; and (7) Good handling and storage equalities of the fruit.

The accompanying drawing shows typical specimens of the fruit and foliage of my new variety, with certain of the fruit specimens shown in cross section to expose the stone and the pit cavity, respectively, as well as other fruit specimens and stones shown in elevation to illustrate the shape and external appearance thereof, all as depicted in color as nearly true as it is reasonably possible to make the same in a color illustration of this character.

The following is a detailed description of my new variety, with color terminology in accordance with Maerz and Paul's Dictionary of Color, except where general color terms of ordinary dictionary significance are obvious:

Parentage: Sport of "Le Grand."

Propagation: Holds its distinguishing characteristics through succeeding propagations by budding.

Locality where grown and observed: Near Visalia, Tulare County, California.

Tree:

*Trunk.*—Large.

*Branches.*—Good thickness. Color: old wood—varies from Domingo Reddish Brown, Plate 7H8 in 2-year wood to Bonito Fuscuous Grey, Plate 7A7 in 4-year wood; new wood—upper side Oasis Green, Plate 20L2, shading to Corinthian Red, Plate 5J2 on parts of under side.

*Lenticels.*—Many; large.

*Leaves.*—Mostly fairly smooth, but many crinkly and wavy, and many slightly rolled inward from edge. Margin—crenate; large. Size—large. Length—many over 6 inches long. Width—from 1½ inches to 1¾ inches. Base angle—mostly broadly acute. Apex angle—mostly acuminate. Color: dorsal side—Elm Green, Plate 23J5; ventral side—Calla Green, Plate 22I4, with Linden Green veins, Plate 19J1. Petiole: length—from 11 mm. to 16 mm., but mostly 12 mm.; color—Rainette Green, Plate 21L4. Glands—reiniform; from 2 to 5 in number, but mostly 4. Stipules—none.

Flowers: Self-fruitful; showy; large petals; elongated; edges slightly ruffled.

*Date of first bloom.*—About February 22nd.

*Date of full bloom.*—About March 2nd.

*Buds.*—Large.

*Flower size.*—Large; about 45 mm. in diameter.

*Color.*—From Peach Blossom Pink, Plate 1F2 to France Rose, Plate 1E4 at base.

*Calyx cup.*—From medium to large size; slightly elongated. Color—Andorra, Plate 8L4.

*Calyx lobes.*—Oval; slightly pointed, but rounded at tip.

*Rim of receptacle.*—Color—France Rose, Plate 1H4.

*Filaments.*—Color—from Bachelor Button Red, Plate 3B4 to Claret Bordeaux, Plate 3K4 at base.

Fruit: Firm; ripens uniformly.

*Ripening date (first picking for shipment).*—About July 21st.

*Size.*—From large to very large, with some medium size. Length—from 2½ inches to 3⅛ inches. Width—from 2⅜ inches to 3 inches.

*Form.*—Longitudinal section—round-ovate. Transverse section—roundish-oblong; mostly elliptical; slightly rounded on the cheeks.

*Suture.*—Mostly very slight depth; more prominent on lip side.

*Cavity.*—Short; wide; deep.

*Apex.*—Mostly rounded and slightly depressed, with apex tip mostly a point in suture depression.

*Base.*—From slightly rounded to flat.

*Stem.*—Thickness—about ⅛ inch. Length—mostly 7/16 inch, with some longer and some shorter.

*Stem scar.*—Medium rounded; adheres strongly to stone.

*Skin.*—Adheres tightly to flesh; greater than average in thickness and toughness.

*Split fruit.*—Few at first picking, with some invisible; no tendency to crack.

*Pubescence.*—None.

*Color.*—Under color of Sunflow Dandelion Yellow, Plate 9L4, overcast with Peppered Red, Plate 4L4, and covered with splotches of Red from China Rose, Plate 5E6 to a full blush of Hydrangea Red, Plate 6L1; with high, waxy gloss.

*Flesh.*—Firm; melting; fibrous. Color—from Pond Lily Yellow, Plate 10I4 to Corinthian Red, Plate 5L2 around pit.

*Juice.*—Abundant.
*Taste.*—Sweet; slightly tart.
*Flavor.*—Very mild.
*Aroma.*—Very slight.
*Fibers.*—Long; thick.
*Eating quality.*—Very good.

Stone:

*Adherence to flesh.*—Cling; many fibers cling to stone.
*Size.*—Mostly large, but few medium. Length—from 1⅜ inches to 1¾ inches, but mostly 1⅝ inches. Width—from 1 1/16 inches to 1 3/16 inches, but mostly 1 3/16 inches.
*Form.*—Mostly obovate.
*Base.*—Large.
*Stem scar.*—Large; oval; deep.
*Apex.*—Wide.
*Edges.*—Even, but dorsal more prominent.
*Surface.*—Pit and line grooves deep and prominent, with some branched.
*Ridges.*—Dorsal— medium height; line markings of medium width and depth. Ventral—medium.
*Color.*—Oak Buff Brown, Plate 13D7, with some stain at base and apex end of Pompeii Red, Plate 7H2.

Resistance to insects and diseases: Comparable to that of the average variety grown and controlled by orchard management practices as determined by comparison with other varieties grown under comparable cultural conditions near Visalia, California.

Keeping quality: Good.

Handling quality: Good.

I claim:

A new and distinct variety of nectarine tree of the yellow-fleshed clingstone fruit type, substantially as herein shown and described, characterized particularly as to novelty by the unique combination of crinkly leaves which have a tendency to roll inwardly along the edges, colorful blossoms, relatively large fruit which sizes and colors rapidly and is highly colored, with the color having a waxy sheen, said fruit being rounded at the base and apex ends but being somewhat elongated, a uniform ripening habit of the fruit, with the ripening period occurring about 10 days to 2 weeks later than the variety "Le Grand" (Plant Patent No. 549) and about 1 week to 10 days earlier than the variety "Late Le Grand" (Plant Patent No. 1,035), and good keeping and handling qualities of the fruit.

References Cited in the file of this patent

UNITED STATES PATENTS

P.P. 1,265 Anderson ---------- Mar. 23, 1954